United States Patent
Karakonstantis et al.

(10) Patent No.: US 9,760,536 B2
(45) Date of Patent: Sep. 12, 2017

(54) METHOD AND APPARATUS FOR LOW COMPLEXITY SPECTRAL ANALYSIS OF BIO-SIGNALS

(71) Applicant: ECOLE POLYTECHNIQUE FEDERALE DE LAUSANNE (EPFL), Lausanne (CH)

(72) Inventors: Georgios Karakonstantis, Trikala (GR); Aviinaash Sankaranarayanan, Madurai (IN); Andreas Burg, Ecublens (CH); Srinivasan Murali, Chennai (IN); David Atienza Alonso, Ecublens (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 216 days.

(21) Appl. No.: 14/421,719

(22) PCT Filed: Aug. 15, 2013

(86) PCT No.: PCT/IB2013/056661
§ 371 (c)(1),
(2) Date: Feb. 13, 2015

(87) PCT Pub. No.: WO2014/027329
PCT Pub. Date: Feb. 20, 2014

(65) Prior Publication Data
US 2015/0220486 A1    Aug. 6, 2015

(30) Foreign Application Priority Data
Aug. 16, 2012 (EP) .................................. 12180712

(51) Int. Cl.
*G06F 15/10* (2006.01)
*G06F 17/14* (2006.01)
(Continued)

(52) U.S. Cl.
CPC .......... *G06F 17/142* (2013.01); *A61B 5/7253* (2013.01); *G06F 17/141* (2013.01);
(Continued)

(58) Field of Classification Search
CPC .... G06F 17/142; G06F 17/141; G06F 17/148; G06F 17/16; A61B 5/7253
(Continued)

(56) References Cited

U.S. PATENT DOCUMENTS

| 4,862,361 A | 8/1989 | Gordon et al. |
| 5,046,504 A | 9/1991 | Albert et al. |

(Continued)

FOREIGN PATENT DOCUMENTS

| WO | WO 01/78290 | 10/2001 |
| WO | WO 2006/032739 A1 | 3/2006 |
| WO | WO 2009/029032 A2 | 3/2009 |

OTHER PUBLICATIONS

AI Maistrou, "Implicit Comparison of Accuracy of Heart Rate Variability Spectral Measures Estimated via Heart Rate and Heart Period Signals," *IEEE Computers in Cardiolology*, 2008.
(Continued)

*Primary Examiner* — Tan V. Mai
(74) *Attorney, Agent, or Firm* — Nixon & Vanderhye P.C.

(57) ABSTRACT

A method and device for reducing the computational complexity of a processing algorithm, of a discrete signal, in particular of the spectral estimation and analysis of bio-signals, with minimum or no quality loss, which comprises steps of (a) choosing a domain, such that transforming the signal to the chosen domain results to an approximately sparse representation, wherein at least part of the output data vector has zero or low magnitude elements; (b) converting the original signal in the domain chosen in step (a) through a mathematical transform consisting of arithmetic opera-
(Continued)

tions resulting in a vector of output data; (c) reformulating the processing algorithm of the original signal in the original domain into a modified algorithm consisting of equivalent arithmetic operations in the domain chosen in step (a) to yield the expected result with the expected quality quantified in terms of a suitable application metric; (d) combining the mathematical transform of step (b) and the equivalent mathematical operations introduced in step (c) for obtaining the expected result within the original domain with the expected quality; (e) selecting a threshold value based on the difference in the mean magnitude value of the elements of the output data vector of the transform said in step (b) and the preferred complexity reduction and degree of output quality loss that can be tolerated in the expected result within the target application; (f) pruning a number of elements the magnitude of which is less than the threshold value selected in step (e); and/or eliminating arithmetic operations associated with the pruned elements of step (f) either in the mathematical transform of step (b) and/or in the equivalent algorithm of step (c).

13 Claims, 5 Drawing Sheets

(51) Int. Cl.
  *G06F 17/16* (2006.01)
  *A61B 5/00* (2006.01)
  *A61B 5/024* (2006.01)
(52) U.S. Cl.
  CPC ............. *G06F 17/148* (2013.01); *G06F 17/16* (2013.01); *A61B 5/02405* (2013.01); *A61B 5/726* (2013.01); *A61B 5/7257* (2013.01)
(58) Field of Classification Search
  USPC ........................................ 708/205, 400–410
  See application file for complete search history.

(56) References Cited

U.S. PATENT DOCUMENTS

| | | | |
|---|---|---|---|
| 5,671,168 | A | 9/1997 | Liu et al. |
| 5,797,840 | A | 8/1998 | Akselrod et al. |
| 7,359,966 | B2 | 4/2008 | Saxena et al. |

OTHER PUBLICATIONS

P. Flachenecker, H.-P. Hartung and K. Reiners, "Power spectrum analysis of heart rate variability in Guillain-Barre' syndrome," *Brain, Oxford University Press*, 1997.
B. S. Saini, D. Singh, M. Uddin, V. Kumar, "Improved Power Spectrum Estimation for RR-Interval Time Series," World Academy of Science, Engineering and Technology, 2008.
S. R. Sridhara et al., "Microwatt Embedded Processor Platform for Medical System-on-Chip Applications", IEEE Journal of Solid-State Circuits, vol. 46, No. 4, Apr. 2011, pp. 721-730.
W. H. Press, G. B. Rybicki, "Fast algorithm for spectral analysis of unevenly sampled data," *Astrophysical Journal*, 1989.
W-C Fang, C-K Chen, E Chua, C-C Fu, S-Y Tseng, S. Kang, "A Low Power Biomedical Signal Processing System-on-Chip Design for Portable Brain-Heart Monitoring Systems," Intern. Conf. on Green Circuits and Systems (ICGCS), 2010.
D. K. Ravish, S. Devi, "Automated Seizure Detection and Spectral Analysis of EEG Seizure Time Series," *European Journal of Scientific Research*, 2012.
C.-C. Chou, S.-Y. Tseng, E. Chua, Y.-C. Lee, W.-C. Fang, H.-C. Huang, "Advanced ECG Processor with HRV Analysis for Real-Time Portable Health Monitoring," *IEEE International Conference on Consumer Electronics*, 2011.
H. Guo, C. S. Burrus, "Wavelet Transform Based Fast Approximate Fourier Transform," *EEE International Conference on Acoustics, Speech, and Signal Processing (ICASSP)*, 1997.
S.-Y. Tseng, W.-C. Fang, "An Effective Heart Rate Variability Processor Design Based on Time-Frequency Analysis Algorithm Using Windowed Lomb Periodogram," *IEEE Biomedical Circuits and Systems Conference (BioCAS)*, 2010.
Kanoun, H. Mamaghanian, N. Khaled, David Atienza,"A Real-Time Compressed Sensing-Based Personal Electrocardiogram Monitoring System," *IEEE DATE*, 2011.
B. Bougard, D. Novo, L. van der Perre, F. Catthoor, "A Wavelet-FFT Based Efficient Sparse OFDMA Demodulator and Its Implementation on VLIW Architecture," *IEEE SiPS*, 2007.
L. Sörnmo, P. Laguna, "Bioelectrical Signal Processing in Cardiac and Neurological Applications," Elsevier, 2005.
Robert S. H. Istepanian, Leontios J. Hadjileontiadis, and Stavros M. Panas, "ECG Data Compression Using Wavelets and Higher Order Statistics Methods," IEEE Trans. on Information Technology in Biomedicine, 2001.
J. P. Martinez et al., "A wavelet-based ECG delineator: evaluation on standard databases," *IEEE Trans. Biomed. Eng.*, vol. 51, No. 4, pp. 570-581, Apr. 2004.
Francisco Rincon, Joaquin Recas, Nadia Khaled, and David Atienza, "Development and Evaluation of Multilead Wavelet-Based ECG Delineation Algorithms for Embedded Wireless Sensor Nodes," *IEEE Trans. on Information Technology in Biomedicine*, 2011.
Acquisition and monitoring of biosignals and physiological parameters, Europe Patent Application P2208PC00, Filed Dec. 20, 2010, Inventors: Nadia Khaled, Hossein Mamaghanian, Francisco Rincón, David Atienza, Pierre Vandergheynst.
International Search Report for PCT/IB2013/056661, mailed Jan. 31, 2014, 6 pages.
Written Opinion of the International Searching Authority mailed Jan. 31, 2014, 7 pages.
Zalay et al., "A Wavelet Packet-Based Algorithm for the Extraction of Neural Rhythms", Annals of Biomedical Engineering, vol. 37, No. 3, Jan. 14, 2009, pp. 595-613.
Hu et al., "A Novel Generic Fast Fourier Transform Pruning Technique and Complexity Analysis", IEEE Transactions on Signal Processing, vol. 53, No. 1, Jan. 1, 2005, pp. 274-282.
Istepanian et al., "ECG Data Compression Using Wavelets and Higher Order Statistics Methods", IEEE Transactions on Information Technology in Biomedicine, vol. 5, No. 2, Jun. 1, 2001, pp. 108-115.
Tseng et al., "An Effective Heart Rate Variability Processor Design Based on Time-Frequency Analysis Algorithm Using Windowed Lomb Periodogram", Biomedical Circuits and Systems Conference, Nov. 3, 2010, pp. 82-85.
Malik, "Heat Rate Variability" European Heart Journal, Jan. 1, 1996, pp. 354-381.

(a)  (b)

METHOD AND APPARATUS FOR LOW COMPLEXITY SPECTRAL ANALYSIS OF BIO-SIGNALS

This application is the U.S. national phase of International Application No. PCT/IB2013/056661, filed 15 Aug. 2013, which designated the U.S. and claims priority to EP 12180712.7, filed 16 Aug. 2012, the entire contents of each of which are hereby incorporated by reference.

0 TECHNICAL FIELD

The present invention relates generally to the analysis of signals and more specifically, to the field of power spectral analysis of bio-signals.

1 BACKGROUND

Power spectrum density (PSD) is a positive real function of a frequency variable associated with a stationary stochastic process describing how the power of a signal or time series is distributed with frequency [1]. The analysis of PSD known as Power Spectral Analysis (PSA) provides a non-invasive means of accessing the physiological and pathological status of a person and is becoming a ubiquitous tool in the diagnosis, prediction and monitoring of various cardiac and brain malfunctions [2-6]. Usually the total low frequency power (LFP) between 0.04 and 0.15 Hz and the total high frequency power (LFP) between 0.15 and 0.4 Hz of cardiac spectra along with their ratio (HFP:LFP) are used as quantitative indicators of various cardiac diseases (i.e., episodic hypertension, sinus tachycardia, bradyarrhythmia, Guillain-Barre syndrome, etc.). Similarly the total power calculated within 3.5-7.5 Hz, 7.5-12.5 Hz and at 12.5 Hz of brain spectra can help in monitoring the brain activity and in diagnosing of epileptic seizures.

By considering the fact that cardiovascular diseases are already responsible for one third of the deaths worldwide, one can easily realize the high value of such a tool in health monitoring [12]. After all the rapid aging of population and prevalence of unhealthy lifestyles is expected to further increase the importance of such applications and need for their integration in our daily portable devices in the near future. Integrating PSA systems within wearable, miniaturized and wireless sensors able to measure and wirelessly report cardiac signals to tele-health providers would enable the required personalized, real-time and long term ambulatory monitoring of chronic patients, its seamless integration with the patient's medical record and its coordination with nursing/medical support. However the high complexity of such applications may hinder their widespread use in particular in portable devices, thus making necessary to devise methods that can reduce their complexity with minimum/no impact on the disease detection capability.

1.1 State of the Art

Traditionally the PSA of Heart Rate Variability involves the extraction of time intervals between successive heart beats (RR intervals) from a continuous ECG of a person and the estimation of a periodogram by using Fast Fourier Transform (FFT) or autoregressive (AR) modeling [2-6]. In these processes, as the RR-intervals are not evenly spaced data, the calculation of PSD requires re-sampling that is usually done by different interpolation methods. However, such methods alter the frequency contents of the signal due to the nonlinear low pass filtering effect [14]. Specifically, if the time series contains inappropriate or missing samples i.e. in heart rate time series, PSD estimates can be severely affected and in such cases resampling is further complicated by the need to infer probable values as replacements.

To circumvent the issues of such methods Lomb periodogram was introduced as a method for deriving the PSD of unevenly spaced data without the need for interpolation and re-sampling [7, 19]. The Lomb method uses least squares fitting to estimate the amplitude of a given sinusoid with angular frequency ωj over non-uniformly sampled data. In other words, the power of the given sinusoid $P_N(\omega_j)$ is computed from the data points using a least squares fit to the model:

$$x(t_i) = A\cos(\omega_j t_i) + B\sin(\omega_j t_i) + n(t_i) \quad (1)$$

for i=0, 1, ..., N, where $n(t_i)$ is noise. As the Lomb method evaluates data and sines and cosines only at times $t_i$ that are actually measured, weighting the data on a "per point" basis rather than on a "per time interval" basis, it is suitable for the analysis of non-uniform data. The Lomb periodogram of a non-periodic signal $x_j$ is given by:

$$P_N(\omega) = \frac{1}{2\sigma^2}\left\{\frac{[\Sigma(x_j-\mu)\cos\omega(t_j-\tau)]^2}{\Sigma\cos^2\omega(t_j-\tau)^2} + \frac{[\Sigma(x_j-\mu)\sin\omega(t_j-\tau)]^2}{\Sigma\sin^2\omega(t_j-\tau)^2}\right\} \quad (2)$$

where μ and σ are the mean and variance of the signal, respectively, $t_j$ is the time interval of the RR sample and the sums are taken over the corresponding window size [11] and τ is a constant offset for each angular frequency ω that makes the periodogram invariant to time-shifts and is given by:

$$\tau = \frac{1}{2\omega}\tan^{-1}\left(\frac{\Sigma\sin 2\omega t_j}{\Sigma\cos 2\omega t_j}\right) \quad (3)$$

While such a method provides theoretically a suitable procedure for estimating the PSA of unevenly data, unfortunately as in the case of FFT and AR methods requires a large number of computations hindering the use of such methods in portable health monitor devices in which power and hardware resources are limited.

The high complexity of the Lomb periodogram, soon led researchers to a modified algorithm for evaluating it, known as Fast-Lomb [8]. The Fast Lomb algorithm as it is called uses the FFT in order to reduce the trigonometric sums in Equation 2 to four simpler sums. Specifically, by defining:

$$S_x = \Sigma x_j \sin 2\omega t_j, \quad C_x = \Sigma x_j \cos 2\omega t_j \quad (4)$$

$$S_2 = \Sigma \sin 2\omega t_j, \quad C_2 = \cos 2\omega t_j \quad (5)$$

then we get an approximation of the original trigonometric sums as:

$$\Sigma x_j \sin\omega(t_j - \tau) = S_x, \quad \Sigma x_j \cos\omega(t_j - \tau) = C_x \quad (6)$$

$$\Sigma \sin^2\omega(t_j - \tau)^2 = \frac{N}{2} + \frac{1}{2}S_2, \quad \Sigma \cos^2\omega(t_j - \tau)^2 = \frac{N}{2} + \frac{1}{2}C_2 \quad (7)$$

Fast Lomb algorithm reduces operations by spreading the input data $x_j$ onto a regular mesh so that $S_x$, $S_2$, $C_x$, $C_2$ can be evaluated using two complex FFTs. Note that even if the method uses FFT, it is in no sense an FFT periodogram but an actual evaluation of Equations 2, 3 with the strengths and weaknesses of the Lomb periodogram.

Fast-Lomb may have reduced the number of computations of original Lomb by approximating the trigonometric sums but unfortunately its complexity remains high hindering in practice the application of real-time PSA on portable devices. Therefore, there is still a need for breakthroughs in order to reduce the complexity and enable the implementation of PSA on battery operated devices [20-24].

A key observation is that the cardiac samples and the resulted RR intervals are approximately sparse in nature and in particular in the wavelet domain. By approximately-sparse we mean that few signal components carry most of its energy. Therefore these few components are also most important for the overall signal quality, while other signal components and the associated computations can potentially be skipped/pruned for a significant complexity reduction. This means that there is room for algorithmic improvements by utilizing the nature of processed heartbeats (RR-intervals) in order to introduce approximations and improve the complexity and battery lifetime of corresponding systems. Such facts were neglected by existing PSA methods described in section 2 and were utilized only for compression of cardiac signals. Specifically not withstanding the high complexity of PSA methods, existing systems utilize the sparsity of raw cardiac signals (ECG) in order to compress them and transmit them wirelessly over an external devise for further processing [12]. While such systems made big steps in allowing the wide usage of such systems to general public they still in no way can be considered as real time cardiac analysis systems, since the analysis and any diagnosis is performed in another external device. In this case the diagnosis of a fatal/risky cardiac event may take part at a stage/time which would be late for the life of the monitored person which could be avoided if real-time PSA was possible. The proposed method combines novel ideas in order to allow the application of real-time PSA on portable devices taking for the first time advantage of the characteristics of the bio-signals and in particular of cardiac signals.

We observed that the core kernel and most computational part of the Fast Lomb algorithm is the FFT. If we could compute FFT such that we could take advantage of the bio-signal characteristics then the Fast Lomb complexity could be reduced substantially. Unfortunately, original Fast Lomb and its core kernel FFT do not take advantage of the specific signal characteristics due to its inherent properties:
  i. In traditional FFT, there is no speed V.S. accuracy tradeoff [9, 10]. In not so rare situations, it is desirable to allow some approximations in order to gain the speed. However, this is not so easy in the classical FFT algorithm. One of the main reasons is that the twiddle factors in the butterfly operations are unit magnitude complex numbers. So all parts of the FFT structure are of equal importance making any approximation in the coefficients risky since they may lead to large accuracy loss. It is hard to decide which part of the FFT structure to omit when approximations are allowed and the speed is crucial. In other words, the FFT is a single speed and single accuracy algorithm.
  ii. Classical pruning methods may help in reducing the complexity of power-hungry FFT, but they do not work well when the few non-zero inputs are randomly located as in RR-intervals. In other words sparse signal does not give rise to a faster FFT algorithm [9].

All the above facts indicate that in order to improve the energy efficiency in such systems an alternative representation, which could expose any hidden signal sparsity and allow approximations is needed.

1.2 Summary of Invention

There are many algorithms in which it is difficult to reduce the complexity and thus the energy without incurring large and even prohibitive quality distortions. The main idea of the invention is to express signals within a target application in a basis in which they exhibit an approximately-sparse representation, thus enabling complexity reduction with minor distortions even in cases that this was not possible before. Specifically, an approximately sparse transformation exposes the significant signal components and allows for the identification and pruning of less-significant computations in subsequent operations in the new basis. Subsequently, this leads to large energy savings with minimum distortions since only the less-significant operations/data that affect the output quality to a minor degree are being pruned.

Methods and apparatus for the complexity reduction and improvement of the energy efficiency of a spectral analysis system, useful in monitoring of various cardiac malfunctions are presented. In our approach the processed signals are expressed in the wavelet domain that enables intelligent energy-quality trade-offs, not available before. Interestingly, the alternative transformation reveals that some signals carry-most of the relevant information, while others influence the output to a lesser extent. Such less-significant signals may be redundant under certain accuracy requirements and thus associated operations could potentially be pruned leading to power savings. To exploit such a property, we adopted threshold rules in the realization of the various algorithmic stages, which allow the static or dynamic pruning of less-useful operations based on the accuracy requirements. The proposed system is implemented on an embedded system simulator and results show up-to 82% energy savings when static pruning is combined with voltage and frequency scaling. In addition, experiments with numerous cardiac samples of various patients show that such energy savings come with a quality loss which does not affect the system detection capability of sinus-arrhythmia.

In a first aspect, the invention provides a method for reducing the computational complexity of a processing algorithm of a discrete signal within an original domain, within a target application, which comprises steps of:
  (a) choosing a domain, such that transforming the signal to the chosen domain results to an approximately sparse representation, wherein at least part of the output data vector has zero or low magnitude elements;
  (b) converting the original signal in the domain chosen in step (a) through a mathematical transform consisting of arithmetic operations resulting in a vector of output data;
  (c) reformulating the processing algorithm of the original signal in the original domain into a modified algorithm consisting of equivalent arithmetic operations in the domain chosen in step (a) to yield the expected result with the expected quality quantified in terms of a suitable application metric;
  (d) combining the mathematical transform of step (b) and the equivalent mathematical operations introduced in step (c) for obtaining the expected result within the original domain with the expected quality;

(e) selecting a threshold value based on the preferred complexity reduction and degree of output quality loss that can be tolerated in the expected result within the target application;

(f) pruning a number of elements from the output data vector the magnitude of which is less than the threshold value selected in step (e); and/or eliminating arithmetic operations associated with the pruned elements either within the mathematical transform of step (b) and/or in the equivalent algorithm of step (c).

In a preferred embodiment of the method for reducing the computational complexity of a processing algorithm of a discrete signal within an original domain, within a target application with minimum or no quality loss:

the said processing algorithm is a discrete Fourier transform;

the said original domain is the frequency domain;

the said target application is the frequency spectrum estimation of a signal;

the said discrete signal is a sampled bio-signal;

in step (a) the wavelet domain is chosen;

in step (b) a discrete wavelet transform converts the discrete signal to the wavelet domain, decomposing the signal into multiple frequency resolutions representing different classes of data by applying a series of suitable high-pass and low-pass filters based on the used wavelet basis;

in step (c) the operations of the original processing algorithm, said to be the discrete Fourier transform, are reformulated by modifying the values of the original Fourier twiddle factors with the values obtained from the frequency response of the high-pass and low-pass filters of the applied wavelet transform;

in step (d) the original signal is processed by the said wavelet transform and its output data vector is processed by the reformulated Fourier operations with the modified twiddle factors;

in step (c) and (d) any quality metric such as the mean square difference between the original expected result and the result obtained after applying the said wavelet transform followed by the said reformulated Fourier operations can be used for quantifying the output quality;

in step (e) and (f) a threshold value is selected such as the data obtained from the said high-pass filters of the applied wavelet transform can be pruned after applying the selected threshold; and in step (g) the operations associated with the pruned high-pass data, in part or as whole, are being eliminated.

In a second aspect the invention provides a method for estimating the frequency spectrum of an original signal, which may be non-uniformly spaced with low complexity, which comprises steps of:

(a) sampling the original signal with a preferred sized window function;

(b) replacing a sampled data value, within the taken window, at an arbitrary point by several data values on a regular mesh in such a way that sums over the mesh are an accurate approximation to sums over the original arbitrary point;

(c) transforming the signal consisting of the extrapolated data samples of step (b) within the taken window in the wavelet domain using a wavelet transform; this step decomposes the signal into multiple frequency resolutions representing different classes of data by applying a series of suitable high-pass and low-pass filters based on the used wavelet basis;

(d) processing the output data vector of the applied Wavelet transform using reformulated Fourier operations with modified twiddle factors, the values of which are obtained from the frequency response of the high-pass and low-pass filters of the applied wavelet transform;

(e) selecting a threshold value such that the data obtained from the said high-pass filters of the applied wavelet transform are pruned after applying the selected threshold;

(f) eliminating the operations associated with the pruned high-pass data of step (e), in part or as whole;

(g) evaluating sine and cosine functions at the times corresponding to the data samples within the taken window using the output data obtained after applying steps (c), (d) and (e);

(h) computing a time shift for each frequency in a desired set of frequencies to orthogonalize the sine and cosine components; and (i) computing the power of each frequency in a desired set of frequencies based on the estimated amplitudes of the evaluated sine and cosine functions.

In a preferred embodiment of the method for estimating the frequency spectrum of an original signal, which may be non-uniformly spaced with low complexity and no or minimum quality loss:

the original signal are time intervals of consecutive heart beats; referred hereafter as RR intervals;

in step (b) the procedure is equivalent to the extrapolation method used in a Fast-Lomb method;

in step (c) the Haar Wavelet Transform with one frequency resolution level is used to transform the sampled data within the wavelet transform;

in step (d) the output data vector of the one-stage Haar Wavelet transform is processed by reformulated Fourier operations with modified twiddle factors, the values of which are obtained from the frequency response of the high-pass and low-pass filters used in the applied Haar wavelet transform;

in step (e) the data obtained from the high-pass filter of the Haar wavelet transform are being pruned in part or as a whole;

in step (f) the operations associated with the pruned high-pass data of step are eliminated, in part or as whole;

in step (h) computing a time shift for each frequency in a desired set of frequencies to orthogonalize the sine and cosine components is equivalent to the time shift applied in a least-squares analysis method and/or a Fast-Lomb method;

in step (i) computing the power of each frequency in a desired set of frequencies based on the estimated amplitudes of the sine and cosine functions is performed as in a least-squares analysis method.

In a preferred embodiment:

the modified twiddle factors of the reformulated Fourier operations that correspond to the frequency response of the low-pass filters used in the applied Haar wavelet transform are sorted based on the their magnitude;

the factors with smaller magnitude than the rest twiddle factors and the associated operations are being eliminated.

In a third aspect, the invention provides a method for estimating the time-frequency distribution of an original signal, which may be non-uniformly spaced with low complexity, which comprises steps of:
(a) recording a signal;
(b) splitting up the recorded signal into overlapping segments;
(c) windowing the overlapping segments;
(d) using a sliding window configuration in order to process the data in different time instances;
(e) applying steps (b) to (i) of claim 3 along with method in claim 4 to compute the frequency spectrum for each segment; and
(f) normalizing each processed segment equally by time-averaging the individual spectrum; achieved by applying a de normalizing factor to each processed segment.

In a fourth aspect, the invention provides a method for analyzing the frequency or time-frequency spectrum of an original signal which may be non-uniformly spaced within a set of desired frequencies with low complexity, which comprises steps of:
(a) estimating the frequency spectrum or time-frequency as in the second or third aspect of the invention;
(b) calculating the ratio between the low frequency power and high frequency power within a set of desired low and high frequencies;
(c) comparing the estimated ratio with a threshold value for evaluating various conditions of interest.

In a preferred embodiment of the invention according to the fourth aspect:
the original signal are time intervals of consecutive heart beats;
in steps (a), the methods as in the second and/or third aspect of the invention are applied for estimating the frequency spectrum;
in step (b) the ratio between the low frequency power and high frequency power within a set of desired low and high frequencies; the desired range being usually 0.04-0.15 Hz for the low frequencies and 0.15-0.4 Hz for the high frequencies;
the differences between the estimated ratio without any pruning and the ratio obtained after applying any pruning described in methods as in the second and/or third aspect of the invention is calculated and used as a quality metric; and
in step (c) the ratio is compared with a proper threshold value in order to indicate any cardiac malfunction.

In a fifth aspect, the invention provides a method for eliminating operations and pruning data, described in the first to fourth aspect of the invention and/or preferred embodiments thereof, comprising:
(a) selecting threshold values based on the differences in the magnitude of the various classes of data in the wavelet domain;
(b) selecting threshold values based on the magnitudes of the twiddle factors that correspond to the frequency response of the filters used Wavelet Transform;
(c) comparing the resulted outputs of the Wavelet Transform with the determined thresholds of step (a) and dropping only those that are less than the determined threshold; and
(d) comparing the computed value in the modified Fourier transform with the determined thresholds of step (b) and dropping only those that are less than the determined threshold.

In a sixth aspect, the invention provides a method for combining the proposed power spectral estimation and analysis described in previous aspects of the invention, with other wavelet based signal analysis and processing tools, and comprising:
(a) sampling the input data within a window;
(b) decomposing the recorded signals by a wavelet transform through the application of filtering operations into multiple frequency resolution levels representing different classes of data;
(c) using the outputs of a preferred frequency resolution level as input to the modified Fourier operations described in above claims;
(d) estimating the power spectra and/or time frequency distribution as described in the second and/or third aspect of the invention;
(e) using the output of the applied wavelet transform for any other signal analysis and processing tool.

In a preferred embodiment of the invention in the sixth aspect:
in step (e) the proposed method is combined with the compression of heart rate data, or extraction of heart characteristics using for instance a wavelet based delineation algorithm;
any pruning of data or elimination of operation described in previous aspects of the invention.

In a seventh aspect, the invention provides a method for re-using the wavelet stages of other cardiac analysis and processing tools with the spectral analysis methods, comprising:
(a) evaluating various wavelet basis for delineation of cardiac data and power spectral analysis;
(b) selecting the wavelet basis that result in large complexity reduction and minor or no loss in output quality of the delineation and spectral analysis algorithms;
(c) using the wavelet transform based on the selected basis for performing both delineation and spectral estimation and analysis of the preferred signal.

In an eighth aspect, the invention provides a device for estimating and analyzing the spectral density in frequency or time-frequency of cardiac signals comprising:
(a) means of recording a signal; which may be non-uniformly spaced;
(b) means of normalizing successive measurements within a window of sampled data;
(c) means of replacing a sampled data value at an arbitrary point by several data values on a regular mesh in such a way that sums over the mesh are an accurate approximation to sums over the original arbitrary point;
(d) means for transforming the signal consisting of the extrapolated data samples of step (b) within the taken window in the wavelet domain using a wavelet transform; this step decomposes the signal into multiple frequency resolutions representing different classes of data by applying a series of suitable high-pass and low-pass filters based on the used wavelet basis;
(e) means for processing the output data vector of the applied Wavelet transform by reformulated Fourier operations with modified twiddle factors, the values of which are obtained from the frequency response of the high-pass and low-pass filters used in the applied wavelet transform;
(f) means for selecting a threshold value such that the data obtained from the said high-pass filters of the applied wavelet transform are pruned after applying the selected threshold;

(g) means for eliminating the operations associated with the pruned high-pass data of step (e), in part or as whole;

(h) means for evaluating sine and cosine functions at the times corresponding to the data samples within the taken window using the output data obtained after applying steps (c), (d) and (e);

(i) means for computing a time shift for each frequency in a desired set of frequencies to orthogonalize the sine and cosine components; and (j) means for computing the power of each frequency in a desired set of frequencies based on the estimated amplitudes of the sine and cosine functions.

In a preferred embodiment:

the determined threshold values mentioned in the eighth aspect are stored within registers; and comparators and multiplexors are used for comparing and pruning and/or eliminating any data and/or associated operation.

In a preferred embodiment, the inventive device further comprises:

means for analyzing the estimated power of each frequency in a desired set of frequencies for determining any health associated issue.

In a ninth aspect, the invention provides the use of the methods from the first to the seventh aspect and device from the eighth aspect for estimating the power spectral density of a bio-signal with low computational complexity and minor or no quality loss;

analyzing the power of a frequency within a set of desired set of frequencies; and monitoring and/or discovering any health issue associated with the analyzed frequencies of the processed signal.

1.3 BRIEF DESCRIPTION OF THE FIGURES

The invention will be better understood in light of the description of preferred example embodiments and in reference to the figures, wherein:

FIG. 1 contains the main idea of finding an alternative signal representation in a preferred domain;

FIG. 2 contains the approach for complexity reduction through an alternative (approximately) sparse representation;

FIG. 3 contains examples of (a) low-pass and (b) high-pass wavelet filter outputs for a Haar based DWT;

FIG. 4 contains DWT-based FFT consisting of two stages i) DWT, ii) Twiddle-factors. Potential data approximated/pruned highlighted with dotted lines;

Figure 7:
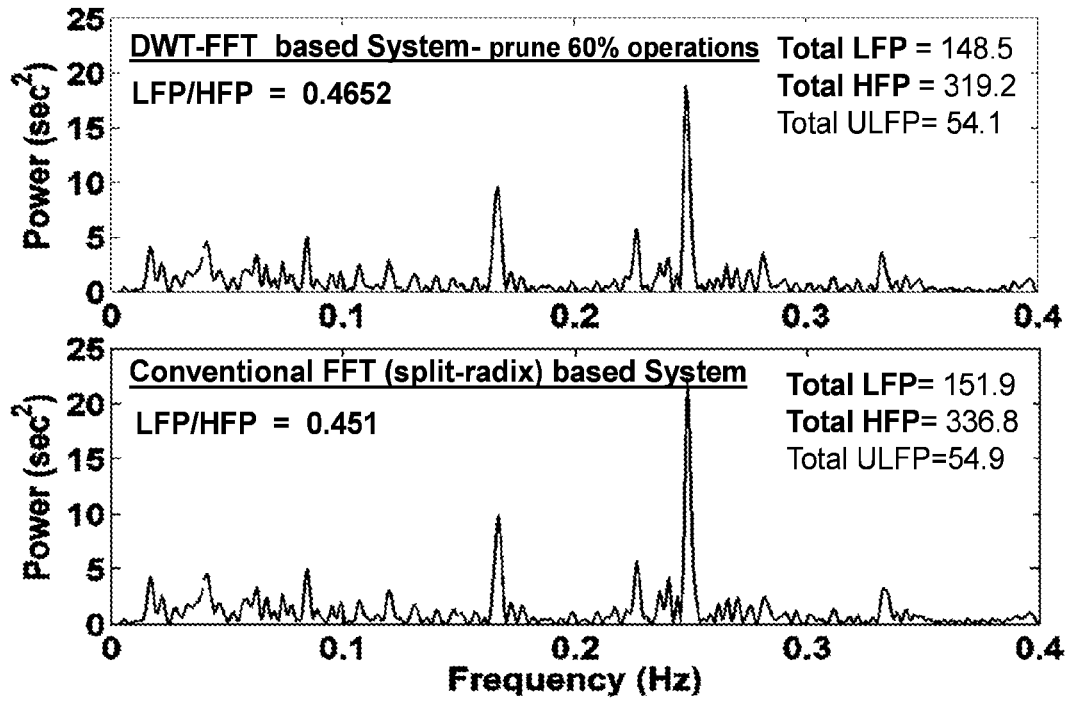
Figure 8:
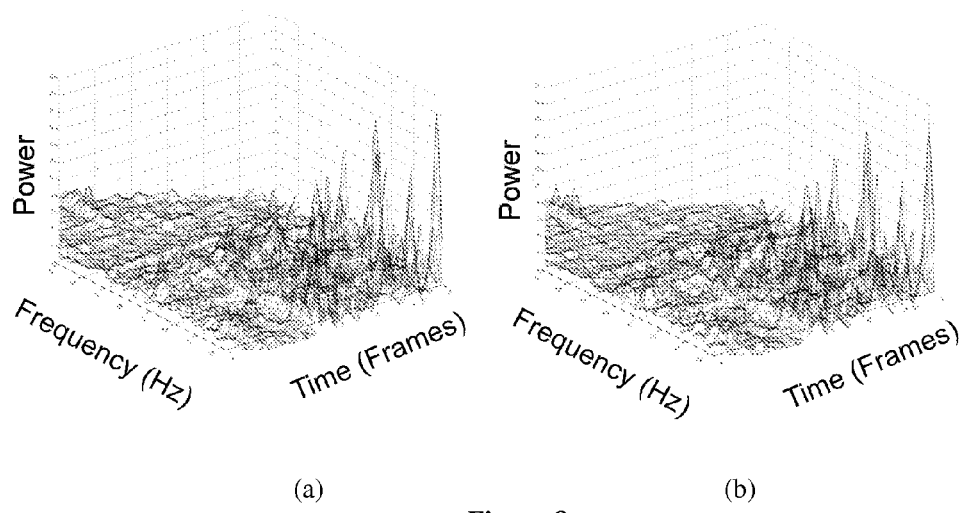
Figure 9:
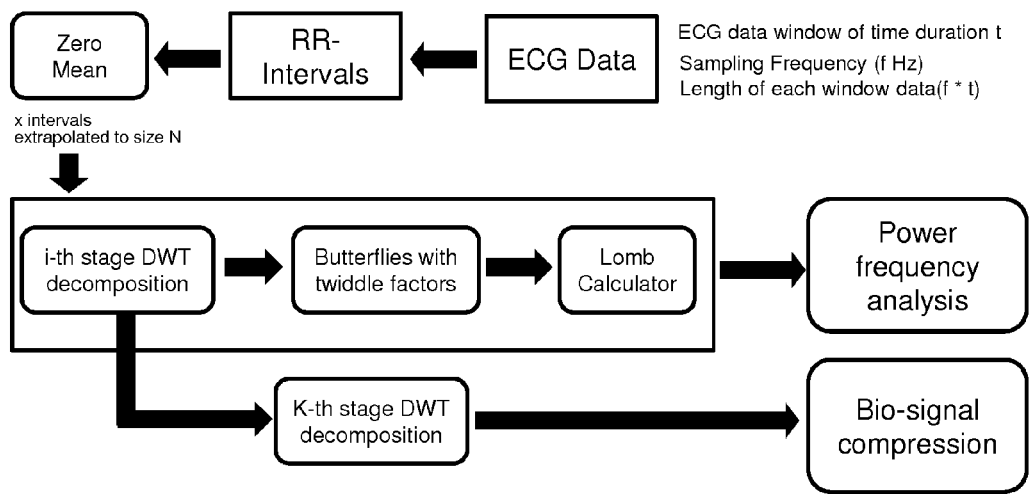

FIG. 7 contains graphs of Power Spectral Analysis—Fast-Lomb. Proposed method result in up-to 81% power savings with only 3% error in LFP/HFP ratio and correct diagnosis of sinus arrhythmia in all samples;

FIG. 8 contains Time-Frequency Analysis over a 1-hour monitoring of a sinus arrhythmia patient using Fast-Lomb periodogram based on (a) conventional FFT, (b) DWT based FFT and approximations of high-frequency components and insignificant twiddle factors; and FIG. 9 illustrates an integration of traditional ECG compression system based on DWT with the proposed spectral analysis device for obtaining simultaneously the compressed signal and the time-frequency analysis.

1.4 DETAILED DESCRIPTION OF EXAMPLE EMBODIMENTS

1.4.1 Complexity Reduction Through Alternative Signal Representations

Changing substantially existing algorithm formulations by considering signal representations in domains where the signal may be (approximately) sparse could allow for a reduction of algorithmic complexity and thus energy.

Figure 1:
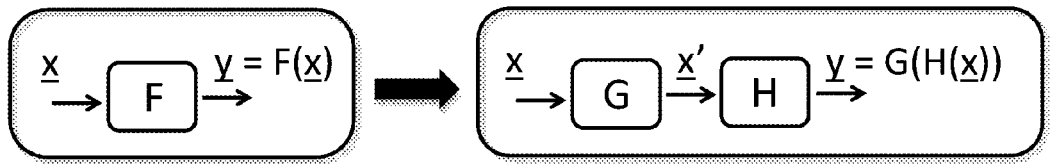

The main idea of the proposed approach is illustrated in FIG. 1. Starting from a function F and a signal $\underline{x}$ the objective is to find a function G that transforms the input signal $\underline{x}$ to a new, equivalent representation $\underline{x}'$, where the signal is approximately-sparse. By approximately-sparse we mean that in the new signal $\underline{x}'$ only few signal components carry most of its energy. Therefore these few components are also most important for the overall signal quality, while other signal components and the associated computations can often be skipped for a significant complexity reduction. In other words, the transformation G not only exposes the unequal significance of different signal components but also allows often identifying the less significant operations in an algorithm enabling a complexity reduction that may have not been possible before. Of course such a transformation G alters the data representation which will also require the reformulation of the function F into an equivalent function H in the sparsity domain to yield the same original result $\underline{y}$. Of course such a representation does not guarantee a reduced algorithmic complexity since we may end up to an overall more complicated algorithm. The key idea to address such an issue is to exploit the introduced approximately sparse signal representation to reduce the algorithmic complexity. This reduction can be achieved by identifying and pruning the less significant computations in the transformations G and H. However, the elimination of computations through artificial sparsification of approximately sparse signals will result in distortions that cause a reduction of the output quality which has to be kept as low as possible. In order to quantify the impact of the introduced approximations on quality we can calculate the error/distortion incurred between the original output signal y=F(x) and the approximated one y'=H(G(x)). Of course the quality metric depends highly on the target application. For instance mean-square-error (MSE)

$$\sigma_p^2 = \|y - y'\|^2$$

and the signal-to-noise-ratio (SNR) might be most appropriate for communications, whereas peak-SNR (PSNR) and ratios between various frequency components are more appropriate in multimedia and biomedical applications. In any case, we need to look for the set of approximated computations that minimize the resulted distortion within any target application.

Figure 2:
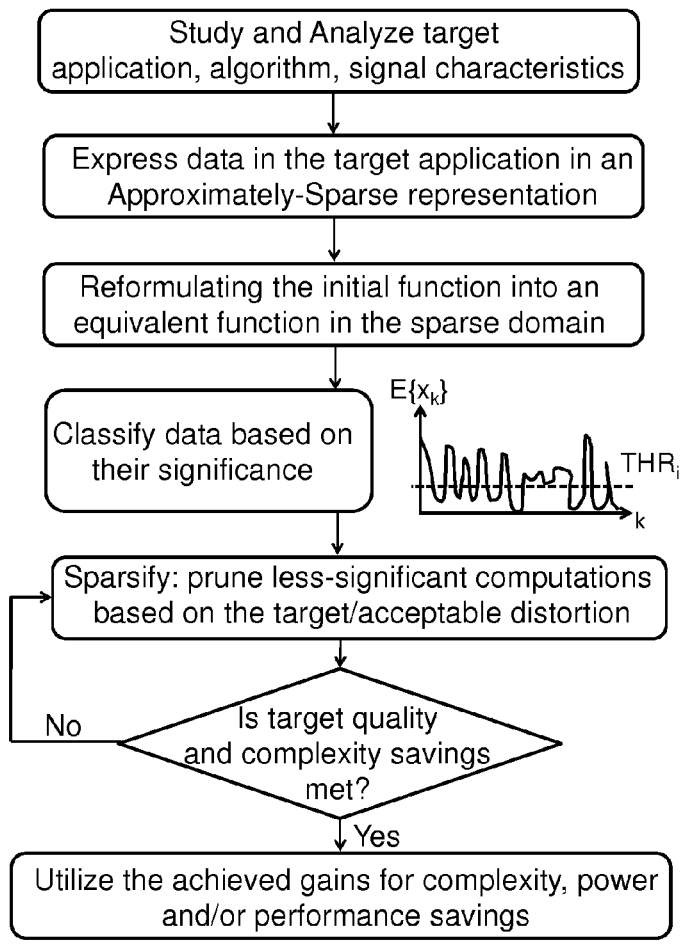

The overall systematic approach to achieve this goal is depicted in FIG. 2. At an initial step we define the type of signals the number and type of coefficients and computations within a targeted algorithm as well as the quality metrics that are of interest in the target application. Next step is to express data on which the target algorithm operates, in an at least approximately-sparse representation. In general, there are many applications in signal processing and communication systems where the signals are approximately sparse in some domain such as time, frequency, or another appropriate basis; in such a representation, most of the samples are at least approximately zero. For instance, Wavelets have an excellent time and frequency localization, which is the main attribute that makes them in general excellent candidate basis for sparsifying signals.

Once the data is available in its approximately sparse representation, we obtain the data statistics of the individual signal components and we perform a sensitivity analysis. For each signal representation under consideration, we introduce a threshold value $THR_i$ to classify signal components into significant and less-significant for example according to:

$$x'_k : \begin{cases} \text{significant,} & \text{if } E\{|x'_k|^2\} \geq THR_i \\ \text{less-significant,} & \text{if } E\{|x'_k|^2\} < THR_i \end{cases}, k = 0, \ldots, N.$$

We then tie all less-significant signal components to zero (sparsification) and prune the associated operations (complexity reduction). By tuning $THR_i$ we maximize the complexity savings while maintaining an acceptable amount of distortion. The output of our method is a set of the required/significant computations that need to be performed to meet the target quality constraint. Based on various quality constraints we can generate different sets which could be used in order to scale the complexity under any energy/quality budget. Note that such sets could be generated by applying static thresholds during design time or on-line by applying dynamic thresholds during operation (i.e., through proper software coding).

1.4.2 Example: Alternative Signal Representation in Frequency Domain

Figure 3:
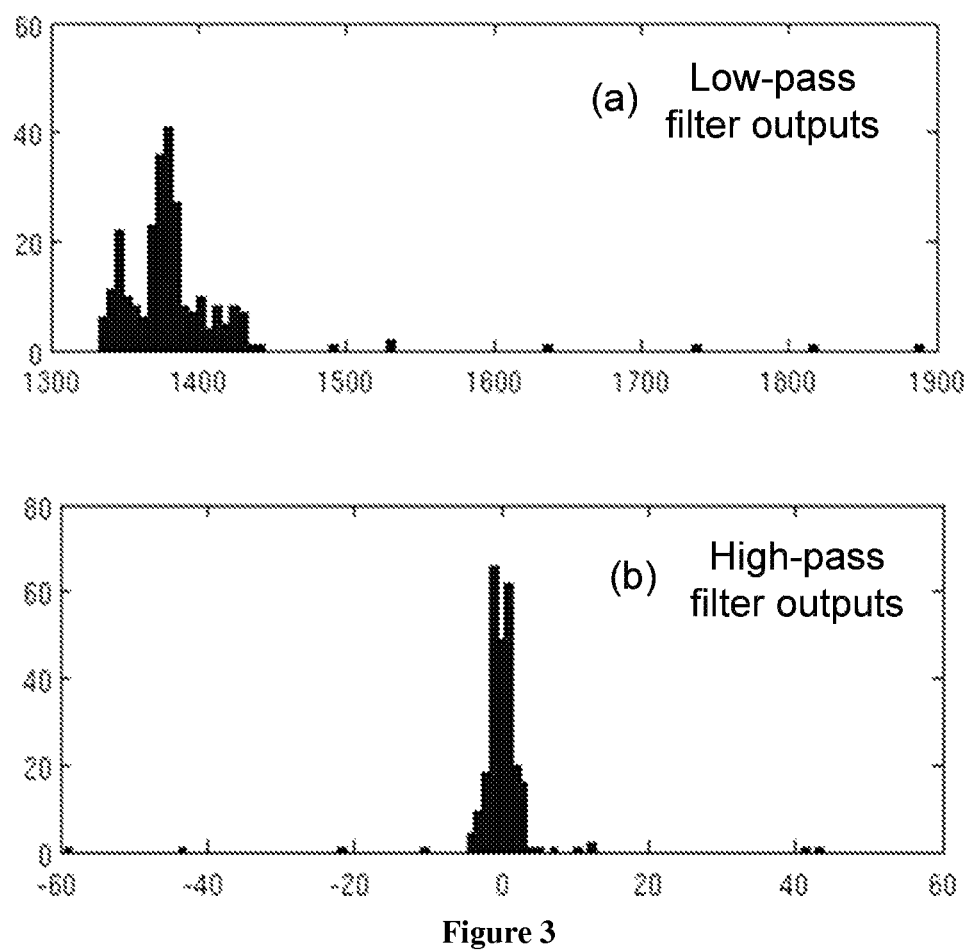

Wavelet decomposition is a special case of sub-band decomposition in which in general the original signal passes through a pair of filters and then is being downsampled by a factor of 2. Given the low pass-filter (LPF) and high-pass filter (HPF) that satisfy the Wavelet constraints, Wavelet decomposition can be compactly expressed as a linear transformation matrix $W_Z$ constructed from LPF and HPF with Z denoting the size of the matrix. The decomposition can then be expressed as:

$$W_Z x = \begin{bmatrix} a_{Z/2} \\ c_{Z/2} \end{bmatrix}$$

where $a_{Z/2}$ and $c_{Z/2}$ is the decomposed low-pass and high-pass signal, respectively. Discrete Wavelet Transform (DWT) consists of one or more stages depending on the degree of the desired resolution and each of them contain a HPF and LPF that compute the so-called approximation and detail coefficients, respectively. Note that the filter order depends on the basis of the mother Wavelet used, i.e., Haar, Db2, Db4 etc. ..... Interestingly, after processing extrapolated RR-intervals of numerous heart samples (FIG. 3(a)) with DWT of various known basis (i.e., Haar, Db2 and Db4) we observed that the two output bands of high and low frequencies differ significantly in terms of their magnitude. Specifically, we observed that the HPF outputs were distributed around zero (FIG. 3(b)) indicating that such parts could be pruned for complexity reduction with potentially minimum impact in quality. In other words, RR-intervals are approximately-sparse in the Wavelet domain, which can be utilized for achieving complexity reduction.

Based on the above analysis DWT provides an alternative transformation (say W) that expresses the input signal x (RR-intervals) with an approximately-sparse representation x'. However, such a transformation W alters the initial data representation which requires the reformulation of the initial function of FFT (say F) into an equivalent function (say G) in the sparsity domain to yield the original expected result $\underline{y}$:

$$\underline{y} = F(\underline{x}) \Longleftrightarrow \underline{y} = W(G(\underline{x})) \tag{8}$$

Figure 4:
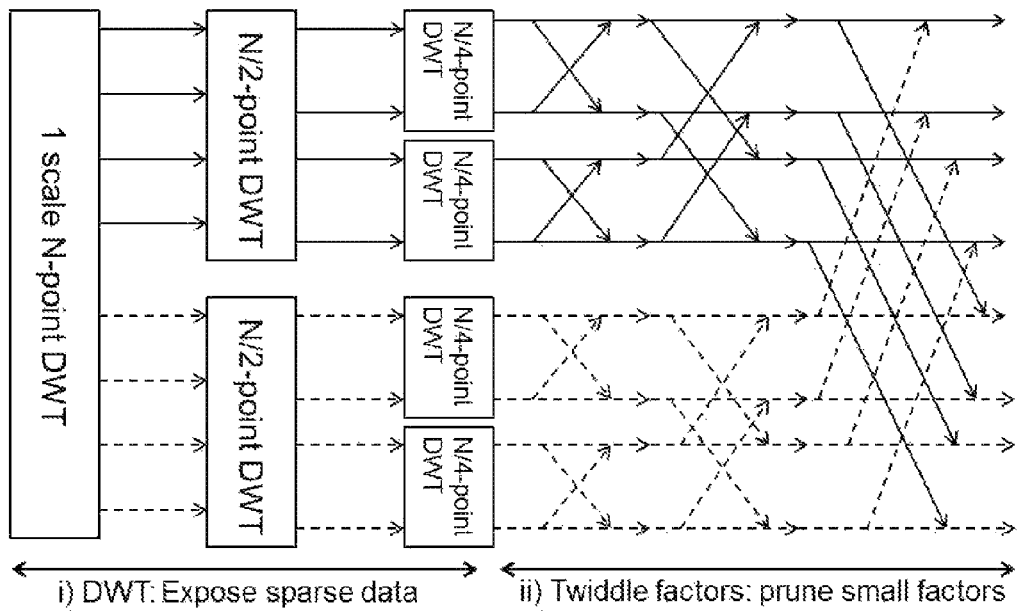

To begin with, the initial algorithm, the FFT can be written in a matrix notation in case of order N as:

$$F_N = F_N \, S'_N \, S_N = \begin{bmatrix} I_{N/2} & T_{N/2} \\ I_{N/2} & -T_{N/2} \end{bmatrix} \begin{bmatrix} F_{N/2} & 0 \\ 0 & F_{N/2} \end{bmatrix} S_N \tag{9}$$

where $T_{N/2}$ is the diagonal matrix with twiddle factors on the diagonal and $S_N$ is an N×N even-odd separation matrix. The first part of the new transform, the DWT $W_N$, obeys $W'_N W_N = I_N$ since it is an orthogonal linear transformation. Based on this property the Fourier transform can be written as $F_N = F_N W'_N W_N$. Considering also Equation 9, the following factorization can be written:

$$F_N = F_N \, W'_N \, W_N = \begin{bmatrix} A_{N/2} & B_{N/2} \\ C_{N/2} & D_{N/2} \end{bmatrix} \begin{bmatrix} F_{N/2} & 0 \\ 0 & F_{N/2} \end{bmatrix} W_N \tag{10}$$

where $A_{N/2}$, $B_{N/2}$, $C_{N/2}$, $D_{N/2}$ are all diagonal matrices, which was also mathematically proven in [15] but its use was very limited up-to now. The values on the diagonal of $A_{N/2}$ and $C_{N/2}$ correspond to the length-N DFT of the lowpass filter of the wavelet transform, whereas the values on the diagonal of $B_{N/2}$ and $D_{N/2}$ are the length-N DFT of the highpass filter of the wavelet transform. The factorization shown in Equation 10 suggests a DWT based FFT algorithm, whose block diagram for an order of N=8 is depicted in FIG. 4. The algorithm consists of 2 main stages; the highpass and the lowpass DWT outputs go through separate length-4 DFT, and then they are combined with butterfly operations. The same scheme can be iteratively applied to shorter length DFTs (i.e., 4-point) to get the full DWT based algorithm. The full system is equivalent to a binary tree wavelet packet followed by modified FFT butterfly operations, where the twiddle factors are the frequency response of the wavelet (lowpass and highpass) filters. The overall process represents a new transformation with the distinguished processes W (DWT) and G (butterflies with new twiddle factors) we looked for in Equation 8.

Interestingly, no one had utilized it in order to take advantage of its properties. The main reason for that is the fact that the complexity of the algorithm is much more than the original FFT for a given order N. In particular, we evaluated the complexity of the algorithm with N=512 using various wavelet bases (i.e. Haar, Db2, Db4) and compared it with one of the fastest known FFT implementations known as split-radix FFT. Results show that (without pruning or exploitation of the sparsity of the signal) the wavelet-based FFT comes with 36%, 49%, or 76% increased computations compared to the split-radix FFT in case of Haar, Db2, and Db4 DWT bases, respectively. Therefore, there is a need for tuning various parameters in order to reduce the complexity of the algorithm and adjust it for the specific application.

While in many applications the processed signals are random in nature and most importantly do not carry any inherent information that allow the reduction of computations with minimum impact at the output quality [13] we found that the nature of the bio-signals and in particular of cardiac signals [14] would be an excellent signal space that could get advantage of the properties of an alternative representation in frequency domain. By representing the bio-signals within the wavelet domain wherein they are approximately sparse and pruning the most suitable data/ operations we achieve to reduce substantially the complexity of algorithms/applications functioning in the frequency domain such as the power spectral analysis of bio-signals needed in the monitoring of health issues.

1.4.3 Power Spectral Analysis System

Figure 5:
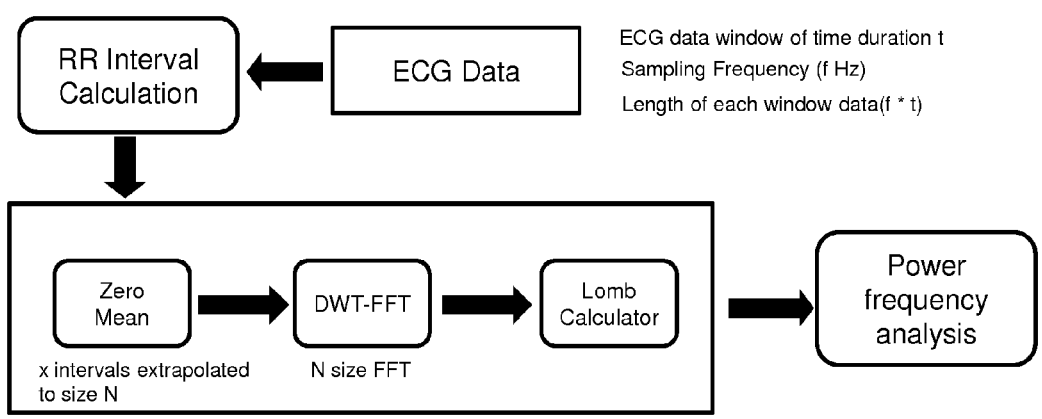
FIG. 5 shows an Overall System for PSA of HRV.

The overall system for performing PSA of ECG data is shown in FIG. 5. Initially, the ECG data are being recorded with a sampling frequency f and based on a fixed widow size the data are being sent for RR interval calculation for which various low complexity methods exist. Next since we perform the evaluation for each window, in order to normalize the data, we calculate the zero mean of the RR intervals and based on the number of intervals we extrapolate them to size n in order to meet the fixed size N of FFT block. After extrapolating the RR-intervals the DWT based FFT that is described above is used to calculate the trigonometric coefficients that are used in equations 2 to 7 to calculate the power spectrum of the window data. The ECG data is sent in different windows and the HRV analysis is performed for every window to provide real time information for portable monitoring devices. Windows could be overlapped up-to 50% in conventional Fast Lomb based PSA. As shown in FIG. 5 the power spectrum is calculated using Equation 2 to 7 described above.

Interestingly, the first stage of the FFT-DWT (DWT-decomposition) algorithm makes this type of signals sparse separating them into significant (high-values) and less-significant (low-values) which can ultimately be dropped as highlighted in FIG. 4. This can be attributed to DWT properties and its excellent time and frequency localization. Actually, each DWT stage by applying a highpass and a lowpass filter computes the so-called approximation and detail coefficients, respectively containing a percentage of the initial signal energy. As the stages (known as scales) increase the frequency (low frequencies) and time (high frequencies) resolution increases. Such a property was used traditionally by many signal analysis algorithms including the RR-interval extraction in order to extract the required information. However, usually such a process requires many stages (i.e. more than 8) and complex Debauchees basis (i.e. db6) and thus was not favored from a practical/cost viewpoint. Nonetheless, one of the popular applications of DWT in cardiac analysis was the data compression which is applied in order to compress the recoded ECG data from a wearable sensor and send them wirelessly to another more capable device for further analysis. The main reason for that is the fact that the time domain and most importantly frequency domain analysis is performed by complex algorithms as we discussed above that need high performance and energy resources which could not be provided by a wearable device.

To this end, the proposed system could reduce the complexity of PSA algorithms and allow real time processing and in time detection of any malfunction. While researchers have taken already advantage of the fact that ECG data are sparse in nature and thus they can be compressed by an approximate representation in the wavelet domain [12] none have thought up-to now to utilize this property in the analysis algorithms.

1.4.4 Proposed Complexity Reduction

As we discussed an alternative signal representation that exposes the hidden signal sparsity in wavelet domain is possible. However, as we noticed such a representation does not guarantee a reduced algorithmic complexity since it ends up to an overall more complicated algorithm. The key idea to address such an issue is to exploit the introduced approximately sparse signal representation to reduce the algorithmic complexity as we discussed in 1.4.2. This reduction can be achieved by identifying and pruning the less significant computations that affect the output quality/accuracy to a small extent in the transformations W and G. This is achieved by obtaining the data statistics of the individual signal components and applying a threshold value $THR_i$ to each stage for classifying components into significant and less-significant. For instance, in the first stage, DWT transforms the input signal x into x' in which two energy bands (HPF and LPF outputs) can be distinguished as we showed in FIG. 3. Thus by applying a $THR_1$ we could distinguish components into significant and less significant, i.e. according to:

$$x'_k : \begin{cases} \text{significant}, & \text{if } E\{|x'_k|\} \geq THR_1 \\ \text{less-significant}, & \text{if } E\{|x'_k|\} < THR_1 \end{cases}, k = 0, \ldots, N \quad (11)$$

By tying then all less-significant signal components to zero (sparsification) and pruning the associated operations we could achieve complexity reduction. Similarly, by applying a threshold in the second stage of the butterfly operations on the twiddle factors we could further reduce the overall number of operations as we discuss in the following subsections. Note that by tuning $THR_i$ we can obtain trade-offs between complexity reduction and distortion which need to be kept as low as possible. The distortion introduced by the proposed approximations is quantified by evaluating the mean-square-error (MSE) between the original output signal y=F(x) and the approximated one y'=W(G(x)) along with the overall impact on the ratio R=LFP/HFP that as we discussed indicates the detection capability of cardiac malfunctions.

1.4.5 Signal Sparsification—Band Pruning

As we discussed in Section 3 the first stage of the new formulation is the DWT, which after processing the RR-intervals it distinguishes the signal into two groups/bands; the high energy (LPF outputs) and the low energy (HPF outputs) bands. Based on such differences the highpass-detail computations associated with the less-significant signal components can be pruned, eliminating the corresponding half band of the DWT as highlighted in FIG. 4. By doing so the multiplications and additions associated with the dropped signals in the second stage of the wavelet-based FFT can also be pruned as shown in FIG. 4. After the applied signal sparsification and the associated pruning of operations, the new sparse wavelet-based FFT process ($F_{N\_SP}$) can be written as:

$$F_{N\_SP} = F_N W'_N W_N = \begin{bmatrix} A_{N/2} & 0 \\ C_{N/2} & 0 \end{bmatrix} \begin{bmatrix} F_{N/2} & 0 \\ 0 & 0 \end{bmatrix} W_N \quad (12)$$

where $F_{N/2}$ along with factors $B_{N/2}$ and $D_{N/2}$ are set to zero due to their insignificant content.

We now repeat the complexity comparison and we observe that the number of computations is reduced by 28%, 21%, and 8% compared to the split radix FFT if the Haar, the Db2, or the Db4 are used as DWT basis, respectively.

Overall, we determined that by using Haar as the DWT basis and applying only one stage of DWT decomposition is sufficient for separating the energy of the processed data to the required approximation level leading to an end-result with minimum error (not affecting any diagnosis) with low complexity. While we could further decompose the lowpass-detail data further by applying more DWT stages as in conventional data analysis algorithms, we found that this is not necessary and rather costly. Specifically, as we discussed in PSA what matters are the values of HPF and LPF and the ratio between them rather than the increased time and frequency resolution that could be achieved by more DWT stages. Therefore, our algorithm utilizes the property of DWT at minimum cost (by using the low cost Haar basis and only one stage decomposition) in order to reduce the complexity and prune any insignificant information from the first DWT stage.

1.4.6 Twiddle-Factor Pruning

Figure 6:
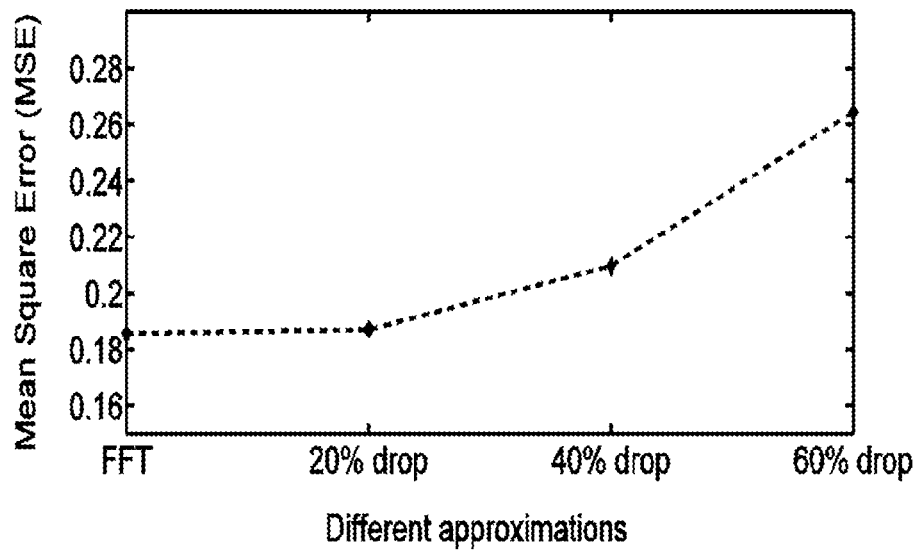
FIG. 6 shows Mean Square Error (MSE) for various $2^{nd}$ stage approximations.

In the second stage of the algorithm, the DWT outputs are multiplied with twiddle factors that are the frequency response of the filter coefficients of the chosen wavelet basis (Haar, Db2, Db4 etc.). Such factors carry the unique property that they do not lie on the unit circle but they differ in their magnitude substantially as opposed to the FFT twiddle factors. This exactly property is being exploited to introduce another novelty in our approach that is the exclusion of the computations based on small magnitude twiddle factors. Specifically, we observe that the twiddle factors $[A_1, A_2 \ldots A_{N/2}]$ decrease in magnitude $(A_1 > A_2 \ldots > A_{N/2})$, whereas factors $[C_1, C_2 \ldots C_{N/2}]$ increase in magnitude $C_1 < C_2 < \ldots < C_{N/2}$. In particular, factors $A_{N/2}$ and $C_1$, $C_2$ etc. have a small magnitude (close to zero). This indicates that the operations associated with these small factors might also influence the output result to a lesser extent. To determine the significance of its factor and of the associated operations we performed a sensitivity analysis by pruning various small factors (which we can term as less-significant) and observed the impact on output quality. Based on our analysis we have generated 3 sets of factors based on their magnitudes and the number of pruned computations that can be achieved (i.e Set1 corresponds to 20% pruned factors/operations, Set2 to 40%, and Set3 to 60%). Our results (FIG. 6) show that the output quality in terms of MSE decreases slightly compared to the conventional FFT outputs if we apply the above approximations to the $2^{nd}$ stage of the algorithm but such distortions do not affect the capability of the system in detecting any arrhythmia. The approximations of the twiddle factors $[A_1, A_2 \ldots A_{N/2}]$ and $[C_1, C_2 \ldots C_{N/2}]$ in a matrix form is shown next:

$$F_{N\_SP} = \begin{bmatrix} A_{N/2} & 0 \\ C_{N/2} & 0 \end{bmatrix} \begin{bmatrix} F_{N/2} & 0 \\ 0 & 0 \end{bmatrix} W_N = \begin{bmatrix} \begin{bmatrix} A_1 & \cdots & 0 \\ \vdots & \ddots & \vdots \\ 0 & \cdots & A_{N/2} \end{bmatrix} & 0 \\ \begin{bmatrix} C_1 & \cdots & 0 \\ \vdots & \ddots & \vdots \\ 0 & \cdots & C_{N/2} \end{bmatrix} & 0 \end{bmatrix} W_N$$

Note also that as the wavelet basis and thus filter sizes increases (i.e. in case of Db4), the number of small-valued/zero twiddle-factors is also increasing. However, at the same time the number of computations in the DWT stage is also increasing. Therefore, there is a clear trade-off between the approximations applied in the second stage and the number of computations in the DWT stage. Overall, we observed that the proposed approximations can reduce by 52% the number of additions and 17% the multiplications compared to a conventional split-radix FFT algorithm. Note that the savings increase with the order (i.e. in case of N=1024 then we obtain we obtain further 12% less multiplications and 8% less additions) due to the logarithmic complexity growth of original FFT with the order.

TABLE I

LFP:HFP ratio under static and dynamic pruning

| LFP/HFP Ratio | Orig. FFT based PSA | PSA based on prop. FFT with $1^{st}$ stage approx. and various approx. in $2^{nd}$ stage | | |
|---|---|---|---|---|
| | | $1^{st}$ stage band drop | Set1 | Set2 | Set3 |
| Static Pruning | 0.45 | 0.465 | 0.465 | 0.483 | 0.492 |
| Dynamic Pruning | 0.45 | 0.465 | 0.467 | 0.47 | 0.471 |

1.4.7 Energy-Quality Trade-Offs Through Static and Dynamic Pruning

In order, to evaluate the energy savings and the distortions obtained by the proposed approximations we have mapped the conventional and new PSA system on a single-core processor simulator [12]. In addition, we analyzed numerous sinus-arrhythmia samples (that is one of most common arrhythmia conditions) from PhysioNet database and we evaluated the ratio between the low frequencies power (LFP) (0.04-015 Hz) and the high frequencies power (HFP) (0.15-0.4 Hz) of the heart rate spectra. This ratio is obtained by processing the outputs of the new FFT using the Lomb calculator and is the most appropriate quality metric for this application. Table 1 depicts the ratio LFP/HFP for the different modes of static approximations where we observe that the ratio remains close to the original value and much less than 1 even when the highpass-band and 60% of twiddle factors are pruned. The resulted PSA based on the proposed approach and the conventional Fast-Lomb method for a sample is depicted in FIG. 7. Interestingly, we can observe that even if we drop 60% of the operations we obtain only 3% difference in LFP/HFP ratio compared to conventional PSA system, thus we can still easily identify the sinus arrhythmia condition.

The proposed approximations result directly in energy savings which can reach up-to 51%. However, such approximations could also be combined with one of the most effective power savings methods that is voltage scaling. In order to determine the degree of voltage scaling that can be applied, we noted the performance improvement that we obtain with the new system that ranges from 40% up-to 51% depending on the degree of approximation. The reduced number of cycles translate directly to throughput/execution-time improvement which can facilitate dynamic voltage and frequency scaling (DVFS). Specifically, the execution time is given by Exec_time=#cycles*freq ($V_{dd}$), where freq. is the frequency of operation which is a function of supply-voltage $V_{dd}$. Based on the improvement in execution we calculated the voltage scaling and the resulted energy savings that can be obtained under various modes of approximations. Interestingly, the proposed approach when combined with DVFS can lead up-to 82% energy savings under the same (acceptable) range of distortions. In the above analysis we have applied fixed number of approximations based on static thresholds that we analyzed during design time. However, it is possible to apply dynamic thresholds during the operation for dynamic pruning of computations. To do so we have altered the application software by including some extra comparison instructions during the $2^{nd}$ computation stage (after the band dropping). Data and twiddle factors that are below a set of thresholds are eliminated on the fly for the various samples. By doing so we could achieve a finer grain approximations, limiting the distortions as shown in Table 1 since only computations that are below a threshold for the specific sample are eliminated. However, the reduction in distortion comes at a cost of an approximately 10% energy overhead compared to the static case and applied DVFS due the extra instructions i.e. comparisons which also limits the degree of the applied voltage scaling. All in all the proposed approach leads to the design of an energy efficient PSA system that could adapt its complexity, energy and performance with minimal and acceptable distortions (ratio always much less than 1).

1.4.8 Time-Frequency Spectral Analysis

Another advantage of our approach is that PSA could be performed in time-frequency space. To be more specific DWT differs from FFT on the fact that it does not only maintains frequency information but also time, therefore HPF and LPF could be evaluated and the time-frequency space providing more accurate information regarding the heart status of a person at various instances of the day. In order to better track the time-varying components of the heart rate, the Lomb periodogram could be modified to be implemented as a time-frequency distribution [11]. Time-frequency analysis using Lomb periodogram could be easily performed by applying a window w(t) to the data and evaluating each segment individually. Using a sliding window configuration w(t−tj) we can obtain the time—frequency distribution $P_N(t, \omega)$. However, as each segment of the window will be variance normalized the time-frequency distribution obtained from the segments will become less meaningful. Thus a method for normalizing each segment equally is needed. In [11] a Welch-Lomb averaged periodogram was utilized. The ability to average variance normalized segments calculated from the Lomb periodogram was achieved through a de-normalizing factor $$\frac{2\sigma}{N}.$$

Using the same technique, we apply this method to denormalize the Lomb periodogram. Thus giving $$P_N(t, \omega) = N \left\{ \frac{[\Sigma\, x'_j \cos\omega(t_j)]^2}{\Sigma \cos^2\omega(t_j)} + \frac{[\Sigma\, x'_j \sin\omega(t_j)]^2}{\Sigma \sin^2\omega(t_j)} \right\} \quad (13)$$

where $x'_j$ is the windowed zero-mean data at time t.

For evaluation of short term HRV, a window of 2 to 5 minutes of RR intervals is suggested. As our target application is for portable monitoring devices where real-time analysis values is more desired, we focus our interest on the low frequencies (LF) and high frequencies (HF) of the heart spectra, which are 0.04 to 0.15 Hz and 0.15 to 0.4 Hz, respectively. Thus, we selected an interval of 2 minutes for the sliding window configuration. Time-frequency analysis of HRV is calculated from RR intervals derived from 2 minutes of ECG data. The optimal overlapping percentage is dependent on usage scenarios and user physiology. Therefore, the amount of overlap is made to be configurable in our system. The overlap in our tests was chosen to be 50% overlap with previous RR interval samples. This configuration was designed so that we are able to obtain a better view of immediate changes in frequency components for normal cases of HRV. FIGS. 8(a) and 8(b) present an example for time-frequency analysis using conventional FFT and DWT-FFT, respectively where it is evident that the results are very similar, irrespective of the approximations applied in case of DWT-FFT based periodogram.

1.4.9 Health Monitoring

Apart from sinus arrhythmia the proposed system can be used for detection and monitoring of many other diseases, including cardiac and neural associated diseases, described below:

In case of Sleep Apnea, the LFP and HFP changes in various sleep stages. The LFP/HFP ratio is maximal during sleep apnea case.

For cases of Congestive Heart Failure, the total power is concentrated at LF range and HFP is virtually absent; these fluctuations help us identify congestive heart failure cases.

For patients with Guillian Bare syndrome, the HFP decreases and the LFP/HFP ratio increases indicating the disease.

For Tachycardia patients, LFP and HFP are considerably decreased when compared to patients with normal heart rates.

In Myocardial infarction, the LFP/HFP is decreased because of an increased HFP.

For Diabetic Autonomic Neuropathy cases, the LFP and Total Spectral power are used to indicate the disease.

For Epileptic seizures, the increase in HFP during the onset of the seizure is used for early detection of epileptic seizures.

1.4.10 System Integration

Another advantage of our approach is that PSA could be performed in combination with other wavelet based analysis and processing methods allowing integration of more systems and thus providing more insight at the health of a person at low cost. We describe two integrated systems next:

a) As we discussed above existing methods of HRV analysis are compressing the recorded signals and extracted RR intervals and transmit them over the wireless channel to an external device in order to perform further analysis [15, 12]. Most of such systems are based on wavelet transform. Usually several stages of wavelet transform and various wavelet bases are applied in order to compress the signal and finally transmit it over the channel to the external device. However, our approach can be combined with the traditional ECG compression methods at low cost and not only compress the signal but at the same time calculate the power spectra at very low cost. This will allow to compress and simultaneously process the ECGs in order to detect any cardiac malfunction. This can be achieved as shown in FIG. 9. The sampled data are being sampled within the fixed window and a wavelet transform of k stages is being applied for compression. Note that the number of stages is being determined by the wavelet basis that is applied (i.e. Haar, Db2, Db4 etc). Out of these successive k stages we obtain the output of the first i stages and use them as input to the $2^{nd}$ stage of butterfly multiplication of our algorithm. Then by applying the required approximations and calculating the lomb factors we obtain the power spectra. The output of the i-th DWT stage is used also as input to compute the rest DWT stages used for compression. In this way we can obtain both the power spectra, time-frequency analysis and the compressed signal.

b) In [17], [18], the authors present a delineation algorithm for finding the different parts of the ECG signal (such as the P, QRS and T waves). This is achieved using a wavelet transformation based algorithm, where the raw ECG signal is transformed using Discrete Wavelet Transforms (DWT). In our proposed method for power spectrum calculations, we also apply the DWT transformation. Thus, we can re-use the wavelet block utilized for the delineation for the power spectral calculations. However, the DWT approach used for delineation may need a different basis of transformation when compared to the power spectrum calculations. To resolve this issue, we can apply a two-step approach: in the first step, we choose the best basis of DWT for waveform delineation and use the same for power spectral calculations. If the results of power spectral calculations are not accurate enough, due to the approximation used in our proposed method, we change the basis in the next step and re-do the calculations. These can be done offline, at design time, and the best basis can be chosen, as a trade-off between delineation quality versus accuracy of power spectral calculations.

1.4.11 Impact—Use of the Proposed Method and Device

Since our novel approaches reduce the computations by more than 75% it allows the implementation of PSA on low-cost wearable devises opening a whole new market and opening new avenues for improving the treatment and health monitoring of each person. The low complexity of the proposed system avoids also the need for transmitting wirelessly the data on external devises for processing the data as it is used to [12], leading to just-in time health monitoring and diagnosis. The system provides an automatic analysis of data to the doctor, preventing him or her from having to work through hours of recorded data and allowing patients to avoid the bulky Holter cardiac monitors which are traditionally worn by patients for around 24 hours at a time. Such a system could measure continuously and remotely, which allows analysis to take place anywhere and detect any anomaly anytime. The World Health Organization estimates that 17 million people die of cardiovascular disease every year. Many of these deaths happen because the type of pathology isn't detected in time. The proposed system could monitor people 24 hours a day, seven days a week at minimum power and cost. Not only will this simplify life for heart patients (less trips to the hospital), but it could also slash costs for healthcare systems. It is certain that such a system could find several health-related uses: monitoring athletic performance, or assessing diet and physical activity in obese patients. Nonetheless, such a system could lead to wearable round-the-clock monitoring devices which could bring new types of analysis, leading to new treatments and ultimately save lives all around the world.

The exciting acceptance of doctors and hospitals of a recent device [12] based on compressing the cardiac data and transmitting them for analysis at a mobile phone indicates that the proposed system by offering the unique characteristic of just in time analysis (without the need of transmitting the data externally for analysis) would be accepted excitingly by the medical and engineering society. Note also that several researchers and companies (i.e. Texas Instruments, USA) [10] recently have tried to implement low power biomedical processors by reducing the complexity of FFT algorithm that was identified as the kernel of many applications but they still did so based on conventional circuit/algorithmic techniques without taking advantage of the characteristics of the bio-signals as we do.

In brief our novel ideas that could widen the use of wearable devices and create new areas of research and products in engineering and medical sciences are:

For the first time we utilize an FFT based DWT algorithm in an application and overcome its practical limitations by utilizing the characteristics of bio-signals in order to apply approximations with minimum quality reduction.

A systematic method is being followed that allowed us to identify the most significant parts in the calculation of an accurate PSD at minimum complexity.

Identify the parts of the algorithm that could be used offering intelligent complexity/power—quality trade-offs that could adapt to the dynamically change of the health status of each person.

Reduce computations by more than 75% with minimum quality reduction and no effect in the correct diagnosis of malfunctions The system can be used for low cost/power power spectrum analysis as well as time-frequency analysis of cardiac (ECG) as well brain (EEG) signals.

The system can be used for the analysis of various other signals where power spectrum density is necessary for the diagnosis or estimation of parameters allowing the implementation of low cost power analyzers that are used in various applications (communications, bio-medical, audio etc).

The proposed spectral analysis device can be combined with existing compression or delineation systems of ECG data based on DWT and provide simultaneously the power spectra within desired frequencies as well as ECG characteristics (QRS complexes, P and T waves) and the compressed ECG data.

The proposed device can serve as a health assessment tool as well as health risk diagnosis tool as it identifies major diseases as well as sleep patterns, fatigue etc.

The proposed device could be useful among professionals from various fields such as Cardiologist, Cardiovascular specialist, Clinical researches, Biofeedback specialists etc.

The proposed device could increase sustainability of health care practices by saving time and money for patients and health care professionals.

The proposed device will be an important tool in identifying online any health issue and help in providing better treatment at the onset of the diseases.

It could be used by companies dealing with athletic equipment, health monitoring, private health institutions and hospitals in order to provide low cost monitoring and treatment solutions.

Note while the proposed approach can be applied for time-frequency spectral analysis of various signals our description mainly focus on cardiac signals.

REFERENCES

[1] A I Maistrou, "Implicit Comparison of Accuracy of Heart Rate Variability Spectral Measures Estimated via Heart Rate and Heart Period Signals," *IEEE Computers in Cardiology*, 2008.

[2] P. Flachenecker, H.-P. Hartung and K. Reiners, "Power spectrum analysis of heart rate variability in Guillain-Barré syndrome," *Brain, Oxford University Press*, 1997.

[3] B. S. Saini, D. Singh, M. Uddin, V. Kumar, "Improved Power Spectrum Estimation for RR-Interval Time Series," World Academy of Science, Engineering and Technology, 2008.

[4] T. Saxena, D. B. Cousins, C. Partridge, W. T. Strayer, "Methods and systems for passive information discovery using Lomb periodogram," U.S. Pat. No. 7,359,966.

[5] W.H. Press, G. B. Rybicki, "Fast algorithm for spectral analysis of unevenly sampled data," *Astrophysical Journal*, 1989.

[6] W-C Fang, C-K Chen, E Chua, C-C Fu, S-Y Tseng, S. Kang, "A Low Power Biomedical Signal Processing System-on-Chip Design for Portable Brain-Heart Monitoring Systems," Intern. Conf. on Green Circuits and Systems (ICGCS), 2010.

[7] D. K. Ravish, S. Devi, "Automated Seizure Detection and Spectral Analysis of EEG Seizure Time Series," *European Journal of Scientific Research*, 2012.

[8] C.-C. Chou, S.-Y. Tseng, E. Chua, Y.-C. Lee, W.-C. Fang, H.-C. Huang, "Advanced ECG Processor with HRV Analysis for Real-Time Portable Health Monitoring," *IEEE International Conference on Consumer Electronics*, 2011.

[9] S R. Sridhara, M. DiRenzo, S. Lingam, S-J Lee, R. Blázquez, J. Maxey, S. Ghanem, Y-H Lee, R. Abdallah, P. Singh, M. Goel, "A Low Power Biomedical Signal Processing System-on-Chip Design for Portable," IEEE Journal of Solid-State Circuits, 2011.

[10] H. Guo, C. S. Burrus, "WAVELET TRANSFORM BASED FAST APPROXIMATE FOURIER TRANSFORM," *EEE International Conference on Acoustics, Speech, and Signal Processing* (*ICASSP*), 1997.

[11] S.-Y. Tseng, W.-C. Fang, "An Effective Heart Rate Variability Processor Design Based on Time-Frequency Analysis Algorithm Using Windowed Lomb Periodogram," *IEEE Biomedical Circuits and Systems Conference* (*BioCAS*), 2010.

[12] K. Kanoun, H. Mamaghanian, N. Khaled, David Atienza, "A Real-Time Compressed Sensing-Based Personal Electrocardiogram Monitoring System," *IEEE DATE*, 2011.

[13] B. Bougard, D. Novo, L. van der Perre, F. Catthoor, "A Wavelet-FFT Based Efficient Sparse OFDMA Demodulator and Its Implementation on VLIW Architecture," *IEEE SiPS*, 2007.

[14] L. Sornmo, P. Laguna, "Bioelectrical Signal Processing in Cardiac and Neurological Applications," Elsevier, 2005.

[15] Robert S. H. Istepanian, Leontios J. Hadjileontiadis, and Stavros M. Panas, "ECG Data Compression Using Wavelets and Higher Order Statistics Methods," IEEE Trans. on Information Technology in Biomedicine, 2001.

[16] J. P. Martinez et al., "A wavelet-based ECG delineator: evaluation on standard databases," *IEEE Trans. Biomed. Eng.*, vol. 51, no. 4, pp. 570-581, Apr. 2004.

[17] Francisco Rincon, Joaquin Recas, Nadia Khaled, and David Atienza, "Development and Evaluation of Multi-lead Wavelet-Based ECG Delineation Algorithms for Embedded Wireless Sensor Nodes," *IEEE Trans. on Information Technology in Biomedicine*, 2011.

[18] Acquisition and monitoring of biosignals and physiological parameters, Europe Patent Application P2208PC0P, Filed Dec. 20, 2010, Inventors: Nadia Khaled, Hossein Mamaghanian, Francisco Rincón, David Atienza, Pierre Vandergheynst

[19] T. Saxena, et al., "Methods and systems for passive information discovery using Lomb periodogram processing," U.S. Pat. No. 7,359,966 B2, 2008.

[20] S. Akselrod, et al, "Apparatus and method for time dependent power spectrum analysis of physiological signals," U.S. Pat. No. 5,797,840 WO, 1998.

[21] S. Akselrod, et al. "Methods and apparatus for monitoring cardiovascular regulation using heart rate power spectral analysis," U.S. Pat. No. 4,862,361, 1989.

[22] D. Albert, P. Lander, "Method and apparatus for analyzing and interpreting electrocardiograms using spectro-temporal mapping," U.S. Pat. No. 5,046,504, 1991.

[23] Anisse Taleb, "Low-complexity spectral analysis/synthesis using selectable time resolution", WO 2009029032 A2, 2008.

[24] Regis Logier, M. Jeanne, Benoit Tavernier, "Method For Processing A Series Of Cardiac Rhythm Signals (Rr) And The Use Thereof For Analysing A Cardiac Rhythm Variability, In Particular For Assessing A Patient's Pain Or Stress," WO/2006/032739.

The invention claimed is:

1. A method for estimating a frequency spectrum of a bio-signal that is non-uniformly spaced with low complexity, the method comprising the steps of:
   (a) sampling the bio-signal with a predefined sized window function;
   (b) replacing a sampled data value, within the window, at an arbitrary point by several data values on a regular mesh in such a way that sums over the mesh are an accurate approximation to sums over the original arbitrary point;
   (c) transforming the signal consisting of the extrapolated data samples of step (b) within the window in the wavelet domain using a wavelet transform by decomposing the signal into multiple frequency resolutions representing different classes of data by applying a series of suitable high-pass and low-pass filters based on the used wavelet basis;
   (d) processing the output data vector of the applied wavelet transform using reformulated Fourier operations with modified twiddle factors, values of the modified twiddle factors are obtained from the frequency response of the high-pass and low-pass filters of the applied wavelet transform;
   (e) selecting a threshold value such that the data obtained from the high-pass filters of the applied wavelet transform are pruned after applying the selected threshold;
   (f) eliminating the operations associated with the pruned high-pass data of step (e), in part or as a whole;
   (g) evaluating sine and cosine functions at the times corresponding to the data samples within the taken window using the output data obtained after applying steps (c), (d) and (e);
   (h) computing a time shift for each frequency in a desired set of frequencies to orthogonalize the sine and cosine components; and
   (i) computing the power of each frequency in a desired set of frequencies based on the estimated amplitudes of the evaluated sine and cosine functions.

2. The method of claim 1, wherein
   the biosignal includes time intervals of consecutive heart beats;
   step (b) includes an extrapolation method using a Fast-Lomb method;
   in step (c) a Haar Wavelet Transform with one frequency resolution level is used to transform the sampled data within the wavelet transform;

in step (d) the output data vector of a one-stage Haar Wavelet transform is processed by reformulated Fourier operations with modified twiddle factors, the values of which are obtained from the frequency response of the high-pass and low-pass filters used in the Haar wavelet transform;

in step (e) the data obtained from the high-pass filter of the Haar wavelet transform are pruned in part or as a whole;

in step (f) the operations associated with the pruned high-pass data of step (e) are eliminated, in part or as a whole;

in step (h) computing a time shift for each frequency in a desired set of frequencies to orthogonalize the sine and cosine components is equivalent to the time shift applied in a least-squares analysis method and/or a Fast-Lomb method; and in step (i) computing the power of each frequency in a desired set of frequencies based on the estimated amplitudes of the sine and cosine functions is performed as in a least-squares analysis method.

3. The method of claim 2, wherein
the modified twiddle factors of the reformulated Fourier operations that correspond to the frequency response of the low-pass filters used in the applied Haar wavelet transform are sorted based on their magnitude; and
the factors with smaller magnitude than the rest of the twiddle factors and the associated operations are being eliminated.

4. The method of claim 1 for estimating the time-frequency distribution of the biosignal that is non-uniformly spaced with low complexity, the method further comprising the steps of:
(j) recording a signal;
(k) splitting up the recorded signal into overlapping segments;
(l) windowing the overlapping segments;
(m) using a sliding window configuration in order to process the data in different time instances;
(n) applying steps (b) to (i) to compute the frequency spectrum for each segment; and
(m) normalizing each processed segment equally by time-averaging the individual spectrum; achieved by applying a normalizing factor to each processed segment.

5. The method of claim 1 for analyzing the frequency or time-frequency spectrum of the biosignal that is non-uniformly spaced within a set of desired frequencies with low complexity comprises the steps of:
(j) estimating the frequency spectrum or time-frequency according to steps (a) to (j);
(k) calculating the ratio between the low frequency power and high frequency power within a set of desired low and high frequencies; and
(l) comparing the estimated ratio with a threshold value for evaluating various conditions of interest.

6. The method of claim 5, wherein
in step (j), the methods are applied for estimating the frequency spectrum;
in step (k) the ratio between the low frequency power and high frequency power within a set of desired low and high frequencies; the desired range being usually 0.04-0.15 Hz for the low frequencies and 0.15-0.4 Hz for the high frequencies;
the differences between the estimated ratio without any pruning and the ratio obtained after applying any pruning calculated and used as a quality metric; and in step (l) the ratio is compared with a proper threshold value in order to indicate any cardiac malfunction.

7. The method of claim 1, further comprising the steps of:
(j) selecting threshold values based on differences in the magnitude of the various classes of data in the wavelet domain;
(k) selecting threshold values based on the magnitudes of the twiddle factors that correspond to the frequency response of the filters used wavelet transform;
(l) comparing the resulted outputs of the wavelet transform with the determined thresholds of step (a) and dropping only those that are less than the determined threshold; and
(m) comparing the computed value in the modified Fourier transform with the determined thresholds of step (b) and dropping only those that are less than the determined threshold.

8. The method for combining the proposed power spectral estimation and analysis according to claim 1 with other wavelet based signal analysis and processing tools, the method comprising:
(j) sampling the input data within a window, the input data representing the biosignal;
(k) decomposing the recorded signals by a wavelet transform through the application of filtering operations into multiple frequency resolution levels representing different classes of data;
(l) using the outputs of a preferred frequency resolution level as input to the modified Fourier operations described in above claims;
(m) estimating the power spectra and/or time frequency distribution in according to steps (a) to (i); and
(n) using the output of the applied wavelet transform for further signal analysis and processing tool.

9. The method of claim 8, wherein
in step (n) the proposed method is combined with the compression of heart rate data, or extraction of heart characteristics using for instance a wavelet based delineation algorithm;
the pruning of data or elimination of operation is applied.

10. A method for re-using the wavelet stages of other cardiac analysis and processing tools with the spectral analysis method of claim 8 comprising:
(o) evaluating various wavelet basis for delineation of cardiac data and power spectral analysis;
(p) selecting the wavelet basis that result in large complexity reduction and minor or no loss in output quality of the delineation and spectral analysis algorithms; and
(q) using the wavelet transform based on the selected basis for performing both delineation and spectral estimation and analysis of the preferred signal.

11. A device for estimating and analyzing the spectral density in frequency or time-frequency of cardiac signals comprising:
(a) means of recording a cardiac signal that is non-uniformly spaced;
(b) means of normalizing successive measurements within a window of sampled data;
(c) means of replacing a sampled data value at an arbitrary point by several data values on a regular mesh in such a way that sums over the mesh are an accurate approximation to sums over the original arbitrary point;
(d) means for transforming the signal including the extrapolated data samples of step (b) within the window in the wavelet domain using a wavelet transform by decomposing the signal into multiple frequency resolutions representing different classes of data by applying a series of suitable high-pass and low-pass filters based on the used wavelet basis;

(e) means for processing the output data vector of the applied wavelet transform by reformulated Fourier operations with modified twiddle factors, values of the modified twiddle factors are obtained from the frequency response of the high-pass and low-pass filters used in the applied wavelet transform;

f) means for selecting a threshold value such that the data obtained from the high-pass filters of the applied wavelet transform are pruned after applying the selected threshold;

(g) means for eliminating the operations associated with the pruned high-pass data of step (e), in part or as whole;

(h) means for evaluating sine and cosine functions at the times corresponding to the data samples within the taken window using the output data obtained after applying steps (c), (d) and (e);

(i) means for computing a time shift for each frequency in a desired set of frequencies to orthogonalize the sine and cosine components; and (j) means for computing the power of each frequency in a desired set of frequencies based on the estimated amplitudes of the sine and cosine functions.

12. The device of claim 11 wherein the determined threshold values are stored within registers; and comparators and multiplexors are used for comparing and pruning and/or eliminating any data and/or associated operation.

13. The device of claim 11, further comprising:

means for analyzing the estimated power of each frequency in a desired set of frequencies for determining any health associated issue.

* * * * *